United States Patent
Chen et al.

(10) Patent No.: US 11,610,677 B2
(45) Date of Patent: Mar. 21, 2023

(54) PATIENT HEALTH MONITORING SYSTEM

(71) Applicant: CHEN TECHNOLOGY, INC., Miami Gardens, FL (US)

(72) Inventors: Christopher Chen, Weston, FL (US); James J. Chen, Miami Gardens, FL (US)

(73) Assignee: Chen Technology, Inc., Miami Gardens, FL (US)

( * ) Notice: Subject to any disclaimer, the term of this patent is extended or adjusted under 35 U.S.C. 154(b) by 65 days.

(21) Appl. No.: 16/212,670

(22) Filed: Dec. 6, 2018

(65) Prior Publication Data

US 2019/0108914 A1 Apr. 11, 2019

Related U.S. Application Data

(63) Continuation-in-part of application No. 14/509,853, filed on Oct. 8, 2014, now abandoned, and a
(Continued)

(51) Int. Cl.
*G16H 50/20* (2018.01)
*G06F 3/04842* (2022.01)
(Continued)

(52) U.S. Cl.
CPC .............. *G16H 50/20* (2018.01); *A61B 5/002* (2013.01); *A61B 5/4842* (2013.01);
(Continued)

(58) Field of Classification Search
CPC ........ G16H 10/20; G16H 40/63; G16H 10/60; G16H 50/20; A61B 5/002
(Continued)

(56) References Cited

U.S. PATENT DOCUMENTS

| 5,583,758 A | 12/1996 | McIlroy et al. |
| 2002/0068857 A1* | 6/2002 | Iliff .......................... G16H 50/20 600/300 |

(Continued)

FOREIGN PATENT DOCUMENTS

WO   WO-0219247 A2 *   3/2002   ........... G06F 19/325

OTHER PUBLICATIONS

Ye, Yinjiao; The role of media health information in individuals' subjective well-being: An exploration of the effects of portrayals of health risks in television news, medical dramas, and pharmaceutical advertising; The University of Alabama. ProQuest Dissertations Publishing, 2006. 3236815. (Year: 2006).*

(Continued)

*Primary Examiner* — Hiep V Nguyen
(74) *Attorney, Agent, or Firm* — DLA Piper LLP

(57) ABSTRACT

Systems, methods, and computer-readable media for analyzing health information to generate medical assessments are described. Health information may include any type of information associated with the health or physical characteristics of a patient. Non-limiting examples of medical assessments include medical diagnoses, medical orders, and risk assessments. A health information analysis system may access health information associated with a patient and provide a medical assessment based on various analyses of the health information. The health information analysis system may receive feedback associated with the medical assessments, such as historical information and/or user input regarding the accuracy or completeness of the medical assessment. The feedback may be used by the health information analysis system to update the analyses of the health information.

5 Claims, 4 Drawing Sheets

Related U.S. Application Data continuation-in-part of application No. 14/456,702, filed on Aug. 11, 2014, now abandoned, and a continuation-in-part of application No. 14/838,087, filed on Aug. 27, 2015, now abandoned.

(60) Provisional application No. 61/888,422, filed on Oct. 8, 2013, provisional application No. 61/946,287, filed on Feb. 28, 2014, provisional application No. 62/042,760, filed on Aug. 27, 2014.

(51) Int. Cl.
  *G16H 50/30* (2018.01)
  *A61B 5/00* (2006.01)
  *G16H 15/00* (2018.01)
  *G16H 10/60* (2018.01)

(52) U.S. Cl.
  CPC .......... *A61B 5/7275* (2013.01); *A61B 5/7282* (2013.01); *G06F 3/04842* (2013.01); *G16H 10/60* (2018.01); *G16H 15/00* (2018.01); *G16H 50/30* (2018.01)

(58) Field of Classification Search
  USPC .......................................................... 705/2
  See application file for complete search history.

(56) References Cited

U.S. PATENT DOCUMENTS

| | | |
|---|---|---|
| 2007/0162295 A1 | 7/2007 | Akhtar et al. |
| 2008/0294507 A1* | 11/2008 | Reiner ................... G16H 15/00 705/7.41 |
| 2010/0222646 A1* | 9/2010 | Rao ........................ G16H 50/30 600/300 |
| 2011/0050702 A1 | 3/2011 | Heimendinger |
| 2013/0006672 A1 | 1/2013 | Dang |
| 2013/0030834 A1* | 1/2013 | Ackerson ............... G16H 10/20 705/3 |
| 2014/0081664 A1 | 3/2014 | Mohlenbrock et al. |
| 2014/0089836 A1* | 3/2014 | Damani ................. G16H 20/40 715/771 |
| 2014/0122096 A1 | 5/2014 | Berry et al. |
| 2014/0164020 A1 | 6/2014 | Thesman |
| 2015/0100344 A1 | 4/2015 | Chen |
| 2015/0248529 A1 | 9/2015 | Chen |
| 2016/0063211 A1 | 3/2016 | Chen |

OTHER PUBLICATIONS

Ash et al., Using Diagnoses to Describe Populations and Predict Costs, Health Care Financing Review (2000), 21(3):7-28.

\* cited by examiner

300

Patient Information
305
Name: _____ DOB: _____
Address: _____ Insurance: _____

Healthcare Provider Information
310
Primary Care Physician: _____ Office: _____
Ordering Physician: _____ Health Care Professional: _____

Patient Vitals and Statistics
315
Height: _____ BP: _____ 352
Weight: _____ Pulse: _____

Physical and Diagnostic Exams
320
General: _____ CT: _____
Abdomen: _____ 354 X-Ray: _____
Heart: _____ Ultrasound: _____

Health Information
325
356
Medications | Diagnoses | Risk Assessments
Medical Orders | Healthcare Providers | Charts

Medical Diagnoses
330
Diabetes
358
Heart Condition

Medical Orders
335
Insulin
Primary Care Follow Up

Risk Assessments
340
85

Healthcare Professional Input
345
Accept  Comments:
Decline

FIG. 3

PATIENT HEALTH MONITORING SYSTEM

CROSS-REFERENCE TO RELATED APPLICATIONS

This application is a continuation-in-part of U.S. patent application Ser. No. 14/509,853 filed Oct. 8, 2014, entitled "PATIENT HEALTH INFORMATION ANALYSIS SYSTEM," which claims priority to U.S. Provisional Application No. 61/888,422 filed on Oct. 8, 2013, entitled "PATIENT HEALTH INFORMATION ANALYSIS SYSTEM," and is also a continuation-in-part of U.S. patent application Ser. No. 14/456,702 filed on Aug. 11, 2014, entitled "HEALTHCARE MANAGEMENT SYSTEM," which claims priority to U.S. Provisional Application No. 61/946,287 filed on Feb. 28, 2014, entitled "HEALTHCARE MANAGEMENT SYSTEM," and is also a continuation-in-part of U.S. patent application Ser. No. 14/838,087 filed on Aug. 27, 2015, entitled "SYSTEMS AND METHODS FOR MODELING MEDICAL CONDITION INFORMATION," which claims priority to U.S. Provisional Application No. 62/042,760 filed on Aug. 27, 2014, entitled "SYSTEMS AND METHODS FOR MODELING MEDICAL CONDITION INFORMATION." The entirety of each is incorporated by reference herein.

BACKGROUND

Hospitals and other types of healthcare facilities generate a large amount of information relating to patients and patient care. This information may be stored in various platforms, such as paper documents (for example, "patient charts" or "patient records") and proprietary electronic records systems. The health information of a typical patient, therefore, is often located in various information storage systems and/or spread across multiple service providers. Thus, it is difficult for a healthcare professional to receive a complete and accurate picture of a patient's medical history. In addition, due to scheduling and resource demands, healthcare professionals generally do not review a patient's complete medical history, even if access to the entire record is available. As such, healthcare professionals often provide diagnoses, health assessments, and medical orders without a full and objective analysis of a patient's collective medical history. Accordingly, healthcare professionals may be able to provide higher quality care more efficiently if they could base their medical decisions on a complete examination of each patient's medical information.

SUMMARY

This disclosure is not limited to the particular systems, devices and methods described, as these may vary. The terminology used in the description is for the purpose of describing the particular versions or embodiments only, and is not intended to limit the scope As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, a health information analysis system may comprise a processor and a non-transitory, computer-readable storage medium in operable communication with the processor. The computer-readable storage medium may contain one or more programming instructions that, when executed, cause the processor to receive health information comprising at least one physical characteristic and at least one symptom associated with a patient analyze the health information using a plurality of assessment rules to generate a medical assessment based on the health information, the medical assessment comprising at least one of a medical diagnosis, a medical order, and a risk assessment, receive feedback associated with the medical assessment, and update the plurality of assessment rules based on the feedback.

In an embodiment, a computer-implemented method for analyzing health information may comprise, by a processor, receiving health information comprising at least one physical characteristic and at least one symptom associated with a patient, analyzing the health information using a plurality of assessment rules to generate a medical assessment based on the health information, the medical assessment comprising at least one of a medical diagnosis, a medical order, and a risk assessment, receiving feedback associated with the medical assessment, and updating the plurality of assessment rules based on the feedback.

In an embodiment, a computer-readable storage medium having computer-readable program code configured to analyze health information embodied therewith may comprise computer-readable program code configured to receive health information comprising at least one physical characteristic and at least one symptom associated with a patient, computer-readable program code configured to analyze the health information using a plurality of assessment rules to generate a medical assessment based on the health information, the medical assessment comprising at least one of a medical diagnosis, a medical order, and a risk assessment, computer-readable program code configured to receive feedback associated with the medical assessment, and computer-readable program code configured to update the plurality of assessment rules based on the feedback.

BRIEF DESCRIPTION OF THE DRAWINGS

The above and other objects of the present invention will become more readily apparent from the following detailed description taken in connection with the accompanying drawings.

FIG. 3 depicts an illustrative health information graphical user interface (GUI) according to some embodiments.

DETAILED DESCRIPTION

Figure 1:
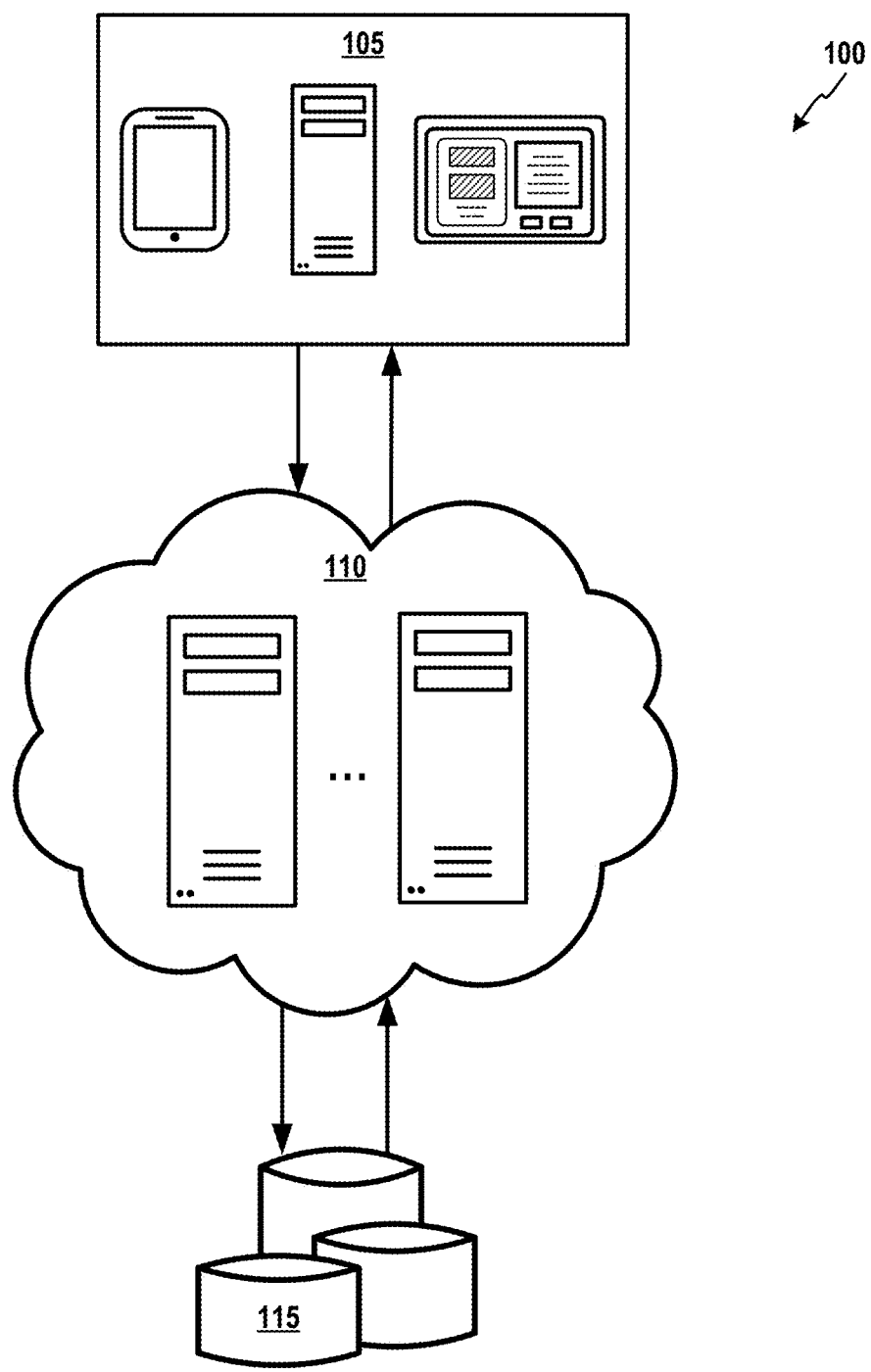
FIG. 1 depicts an illustrative health information analysis system according to a first embodiment.

The described technology generally relates to systems, methods, and non-transitory computer-readable media for analyzing health information. In particular, some embodiments provide a health information analysis system configured to analyze, examine, search, investigate, consider, evaluate, and/or otherwise process health information and to generate various medical assessments based on the health information. Non-limiting examples of medical assessments include medical diagnoses, medical orders, and risk assessments. Health information may include any type of information associated with the health or physical characteristics of a patient, including, but not limited to, name, address, age, gender, demographic information, weight, height, medications, surgeries and other medical procedures (for example, diagnostic tests, diagnostic imaging tests, or the like), occupation, past and current medical conditions, family history, patient description of health condition, healthcare professional description of health condition, and/or symptoms.

The health information analysis system does not automatically provide medical advice, assistance, instructions, or other guidance to patients and/or patient caregivers. As configured according to some embodiments described herein, the health information analysis system may provide information to facilitate efficient access to information and to transform existing healthcare information into a medical assessment that may be used by a healthcare provider and/or a healthcare administrator to manage the delivery of healthcare to patients.

In some embodiments, the health information analysis system may access health information associated with a patient and provide a medical assessment based on various analyses of the health information. In some embodiments, the health information analysis system may receive input from a healthcare provider concerning the accuracy, completeness, correctness, or other measure of a medical assessment for use in determining future medical assessments. In some embodiments, the health information analysis system may be configured to display portions of the health information and/or medical assessments to a healthcare professional. In general, a healthcare professional may include any individual providing healthcare services to a patient, including, without limitation, a doctor, a physician assistant, a nurse, a medical assistant, a medical technician, a patient caregiver, or the like. In such embodiments, the health information analysis system may be configured to differentially display various elements of the health information and/or medical assessments, such as through the use of different colors, in order to highlight, categorize, or otherwise differentiate one or more aspects thereof.

The health information analysis system described according to some embodiments provides multiple technological advantages and technical effects on processes and techniques, including processes and techniques external to the content management system. One non-limiting technological advantage is that the health information analysis system may provide medical assessments to healthcare professionals based on a patient's full medical history, including across healthcare providers and information platforms. Such analyses are not possible using conventional processes and technology because, for instance, they would require too much time to be effective and practical when providing healthcare to patients. Another non-limiting technological advantage is that the health information analysis system is capable of dynamically adapting its analysis processes based on healthcare professional feedback, updated information, or the like. Dynamically adapting medical analysis using such feedback, updated information, or the like is not possible using conventional processes and technology because, for instance, the feedback and/or updated information is not readily available to healthcare professionals in sufficient time or in a format to provide a timely analysis. A further non-limiting technological advantage is that the health information analysis system may present timely and dynamically updated information to medical professionals in a format that is readily comprehensible to provide a timely analysis, including in real-time or substantially real-time. The presentation of health information according to some embodiments allows medical professionals to provide more efficient and effective healthcare to patients compared with conventional techniques and processes that are generally paper-based or use limited graphical user interfaces (GUI) that are not capable of providing a comprehensive and meaningful picture of a patient's health information. A further non-limiting technological advantage is that the health information analysis system may present timely and dynamically updated information to medical professionals in a format that is readily comprehensible to provide a timely analysis, including in real-time or substantially real-time. A still further non-limiting technological advantage is that the health information analysis system may improve methods, rules, algorithms, or other processes for generating medical assessments based on feedback from medical professionals concerning a medical assessment (i.e., whether the medical assessment was accurate, relevant, or the like). In this manner, the health information analysis system is able to provide more accurate, comprehensive, and cost efficient medical assessments compared to those available using existing technology and processes.

FIG. 1 depicts an illustrative health information analysis system according to a first embodiment. As shown in FIG. 1, the health information analysis system (the "analysis system") 100 may include one or more server logic devices 110, which may generally include a processor, a non-transitory memory or other storage device for housing programming instructions, data or information regarding one or more applications, and other hardware, including, for example, the central processing unit (CPU) 405, read only memory (ROM) 410, random access memory (RAM) 415, communication ports 440, controller 420, and/or memory device 425 depicted in FIG. 4 and described below in reference thereto.

In some embodiments, the programming instructions may include a health information analysis application (the "analysis application") configured to, among other things, analyze health information and generate medical assessments. The server logic devices 110 may be in operable communication with client logic devices 105, including, but not limited to, server computing devices, personal computers (PCs), kiosk computing devices, mobile computing devices, laptop computers, smartphones, personal digital assistants (PDAs), tablet computing devices, or any other logic and/or computing devices now known or developed in the future.

In some embodiments, the analysis application may be accessible through various platforms, such as a client application, a web-based application, over the Internet, and/or a mobile application (for example, a "mobile app" or "app"). According to some embodiments, the analysis application may be configured to operate on each client logic device 105 and/or to operate on a server computing device accessible to logic devices over a network, such as the Internet. All or some of the files, data and/or processes (for example, health information, analysis processes, or the like) used for analysis of health information and/or the generation of medical assessments may be stored locally on each client logic device 105 and/or stored in a central location and accessible over a network.

In an embodiment, one or more data stores 115 may be accessible by the client logic devices 105 and/or server logic devices 110. The data stores 115 may include health information, medical assessment information, medical assessment rules, medical assessment processes and/or services, medical information, healthcare facility information, or the like. In some embodiments, at least a portion of the data stores 115 may include information associated with a health information system, including, without limitation, healthcare information and management systems (HIMS), electronic medical record (EMR) systems, radiology information systems (RIS), picture archiving and communications system (PACS), or the like. In some embodiments, the data stores 115 may include information obtained from multiple healthcare facilities and/or healthcare providers. In some embodiments, at least a portion of the data stores 115 may include a third-party data source such as a government healthcare information system (for example, the Centers for Medicare and Medicaid Management (CMS)), a medical library, a third-party medical database, or the like.

Although the one or more data stores 115 are depicted as being separate from the logic devices 105, 110, embodiments are not so limited, as all or some of the one or more data stores may be stored in one or more of the logic devices.

As described in more detail below, the analysis application may access information and/or processes stored in the data stores 115 to generate medical assessments. A healthcare professional may initiate the generation of the medical assessments and/or enter healthcare information from a client logic device 105, and the analysis application may generate a medical assessment for presentation on a display component of the client logic device. For instance, the analysis application may access the health information associated with a patient being evaluated by a healthcare professional and generate medical assessments for consideration by the healthcare professional. For example, the analysis application may provide a medical diagnosis, such as a specific condition that the patient may be experiencing. In another example, the analysis application may provide a medical order, such as a prescription and a diagnostic test for obtaining more information to allow the analysis application and/or the healthcare professional to provide a more complete diagnosis.

Figure 2:
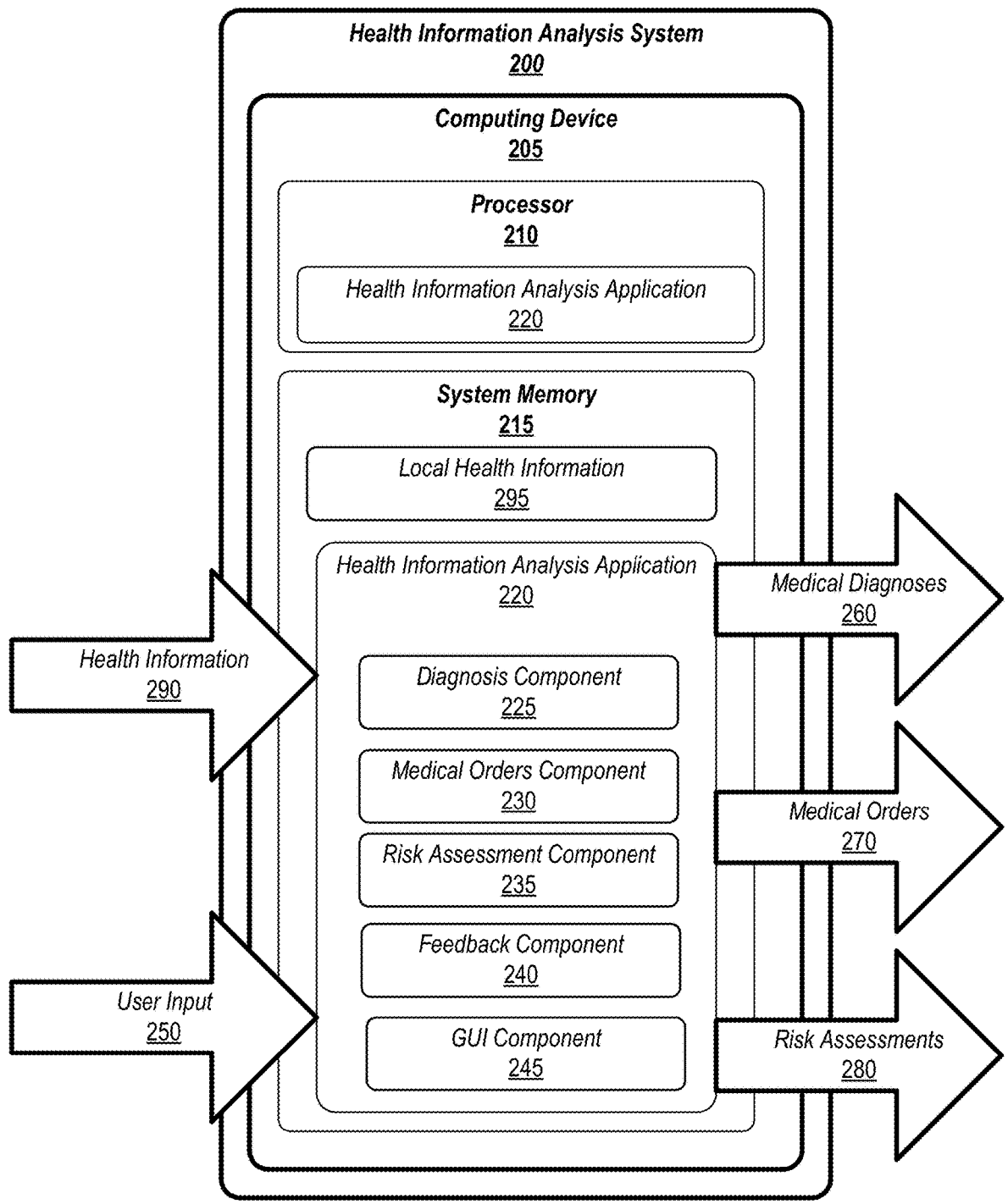
FIG. 2 depicts an illustrative health information analysis system according to a second embodiment.

FIG. 2 depicts an illustrative health information analysis system according to a second embodiment. As shown in FIG. 2, an analysis system 200 may include a computing device 205 having a processor 210 and system memory 215. The computing device 205 may include one or more of any type of computing device, such as the client logic device 105 and server logic devices 110 described in reference to FIG. 1. The processor 210 may be configured to execute an analysis application 220. The analysis application 220 may be configured to receive health information 290 and/or user input 250, for instance, through the processor 210 and/or as stored or cached as local health information 295 in the system memory 215.

The health information 290 may include any information associated with the health of a patient ("health indicators"). Non-limiting examples of such health indicators may include any information associated with a physical condition, a mental condition, symptoms, medical history, medications, family history, diseases, illnesses, conditions, surgeries, medical procedures, medical diagnostic tests, vital signs, lab results, associated healthcare providers, demographic information, allergies, responses to treatment, responses to medication, health information associated with other patients with one or more similar characteristics (for instance, for comparative or analytics purposes). In some embodiments, the health information 290 may include a list of conditions, diseases, injuries or the like (for example, a "problem list") associated with a patient. In some embodiments, the problem list may provide an outline of conditions currently and/or previously affecting a patient. In some embodiments, the health information may include a treatment plan for addressing one or more of the conditions in the list of conditions. Accordingly, the health information 290 may generally include any information capable of being used to generate a medical assessment according to some embodiments described herein.

The analysis application 220 may include various modules, components, programs, applications, routines, functions, processes, or the like to perform functions according to some embodiments described herein. In some embodiments, the analysis application 220 may include a diagnosis component 225, a medical orders component 230, a risk assessment component 235, a feedback component 240, and/or a graphical user interface (GUI) component 245.

The diagnosis component 225 may be configured to automatically process the health information 290 and/or user input 250 to generate a medical diagnosis 260. In general, a medical diagnosis 260 may include identifying a disease, ailment, injury, or other physical or mental condition, and/or one or more causes of any of the foregoing. The diagnosis component 225 may simultaneously process and evaluate all or substantially all of the health information 290 associated with a patient in order to determine potential medical diagnoses 260 indicated by the health information. The diagnosis component 225 may analyze the health information 290 using various algorithms, functions, routines, procedures, rules, or other processes (the "assessment rules") and generate one or more medical diagnoses 260. In some embodiments, the source of the various algorithms, functions, routines, procedures, rules, or other processes may be a third-party source external to the system.

In some embodiments, the diagnosis component 225 may analyze a set of current symptoms to determine one or more medical diagnoses 260. In some embodiments, the diagnosis component 225 may compare the set of current symptoms with past symptoms of the patient and/or other patients to determine one or more medical diagnoses 260. In some embodiments, the diagnosis component 225 may evaluate a patient's family history, physical information (for example, height, weight, or the like), and symptoms to determine one or more medical diagnoses 260. In some embodiments, the diagnosis component 225 may evaluate the user input 250 (for instance, from a healthcare professional treating the patient) in combination with the health information 290 to determine one or more medical diagnoses 260. In some embodiments, the diagnosis component 225 may determine one or more medical diagnoses 260 and may further evaluate the health information 290 to determine possible causes for the medical diagnoses 260.

For example, the diagnosis component 225 may access a patient's list of current medications from the health information 290 and analyze the potential side effects of all of the medications to determine whether one of the medications, a combination of the medications, and/or the medications in combination with one or more physical conditions may be causing certain symptoms. In another example, the diagnosis component 225 may determine that a patient has a certain condition (for instance, diabetes mellitus type 2) and that certain symptoms are likely due to certain patient activity (for instance, diet, taking certain medications, or the like), which may be more likely with patients having the certain condition.

The medical orders component 230 may be configured to generate medical orders 270 based on, among other things, the assessment rules, health information 290, the medical diagnoses 260, and/or the user input 250. In general, medical orders 270 may include any type of directive for a healthcare professional and/or patient for treating, controlling, or otherwise addressing a medical condition (for instance, a medical diagnosis 260). Non-limiting examples of medical orders 270 include orders, instructions, prescriptions, tests, procedures, and recommendations.

In some embodiments, the medical orders component 230 may analyze the health information 290 and/or the medical diagnoses 260 in combination with medical treatment information, for instance, accessible through the data stores 115. For instance, the medical orders component 230 may research, calculate, locate, formulate, or otherwise determine the most effective and efficient medical order 270 for addressing the needs of a patient. The medical orders component 230 may be configured to determine the medical orders 270 in view of a patient's entire medical history, including across healthcare providers, and/or potential treatment costs. In this manner, the medical orders component 230 may take the potential effectiveness, complications and/or the like into account when determining medical orders 270. For instance, the medical orders component 230 may determine that a patient has had the same or similar symptoms related to a medical diagnosis 260 (Diagnosis A) over a five-year period and has been prescribed Medication A and Treatment B (for example, avoiding certain foods). The medical orders component 230 may determine that, although Medication A and Treatment B are the highest recommended treatment for Diagnosis A, the medical order 270 should include prescribing Medication B and further diagnostic testing to see if there are other causes for Diagnosis A. In another instance, the health information 290 may include information that the patient, healthcare facility, and/or healthcare professional have certain preferences for treatments and/or medications. Accordingly, the medical orders component 230 may generate medical orders 270 effectuating such preferences. Non-limiting examples of such preferences may include an approach that prefers changes in a patient's exercise routine and/or diet over prescription of medication, if available; a preference for a certain medication for a particular medical condition; a preference for further diagnostic testing for certain combinations of symptoms and patient histories; a holistic approach; the lowest exposure to radiation or radioactive contrast; and/or the like. In this manner, the medical orders component 230 may ensure healthcare providers are provided with opportunities for more defined care intervention and treatment options.

The risk assessment component 235 may be configured to provide risk assessments 280 associated with a patient and/or a set of patients (for instance, a set of patients with similar health information, including similar demographics, physical measurements, diagnoses, conditions, medical histories, medications, medical procedures, or the like). In some embodiments, the risk assessments 280 may indicate the risk of a patient and/or group of patients for certain medical conditions (for example, a probability of having diabetes mellitus type 2, a probability of surviving a certain condition, a probability of positive treatment outcomes under certain courses of treatment and/or medications, or the like). In some embodiments, the risk assessments 280 may indicate the likely cost of maintaining a patient's health, for instance, based on offering health related services by a healthcare facility and/or healthcare professional.

In some embodiments, the risk assessment component 235 may generate risk assessments 280 based on the health information 290 and the assessment rules for analyzing the health information. For example, the risk assessment component 235 may be configured to score or weigh various elements of the health information 290, such as body mass index (BMI), medical history (for instance, previous or current medical conditions), habits (for instance, diet, exercise, following medical orders 270), likelihood for addiction to certain medications, or the like. The scored health information 290 elements may be used to determine a risk assessment 280 for a patient and/or set of patients. In some embodiments, the risk assessment 280 may include an overall risk assessment for a patient and/or set of patients. The overall risk assessment 280 may be configured to indicate the overall health and/or risk of the patient and/or set of patients (an overall health score). In some embodiments, the risk assessment 280 may include specific risk assessments, such as a heart disease risk assessment, a diabetes risk assessment, or the like.

In some embodiments, the risk assessment component 235 may assign a numerical value, a letter value, or other quantifiable value to the risk assessment 280. In some embodiments, the risk assessment component 235 may categorize the risk assessment 280 as "high," "medium," "low," or some other comparative designation. In some embodiments, the healthcare professional, the diagnosis component 225 and/or the medical orders component 230 may use the risk assessment 280 when determining a medical diagnosis 260, medical order 270, or the like. For example, the diagnosis component 225 may determine that Diagnosis B is more likely for patients with a risk assessment 280 of "high" and that Diagnosis C is more likely for patients with a risk assessment of "medium" or "low." In another example, the medical orders component 230 may generate a medical order 270 including prescribing Medication C for patients with a risk assessment 280 of "low" and Medication D for patients with a risk assessment of "medium" or "high."

In some embodiments, the risk assessment component 235 may use, at least partially, a third-party risk system for determining the risk assessment 280. In some embodiment, the third-party risk system may include the Medicare Risk Adjustment payment model introduced by the Centers for Medicare and Medicaid Management (CMS). In some embodiments, the risk assessment component 235 may take the medical diagnoses 260 for a patient and map them to the Hierarchical Condition Categories (HCC) scores used by the CMS to determine a risk assessment 280 score. In some embodiments, the risk assessment component 235 may use the HCC scores in combination with the health information 290, such as demographic information, past medical information, or the like, to determine a risk assessment 280 score.

In some embodiments, a healthcare professional may accept, deny, provide comments, or otherwise provide user input 250 related to the medical diagnoses 260, medical orders 270 and/or risk assessments 280. In some embodiments, the healthcare professional may add a medical diagnosis 260 to a patient's list of conditions. In some embodiments, the healthcare professional may add a medical order 270 to a patient's treatment plan. The analysis application 220 may receive the user input 250 and store the user input in the local health information 295 associated with the patient and/or modify the medical diagnoses 260, medical orders 270 and/or risk assessments 280 responsive to the user input. In some embodiments, the diagnosis component 225, medical orders component 230 and/or risk assessment component 235 may reevaluate the health information 290 in view of the user input 250 and may potentially generate updated medical diagnoses 260, medical orders 270 and/or risk assessments 280. For instance, the user input 250 may indicate that a patient has a high rate of Condition A in their family, which was not included in the original health information 290 for the patient. The diagnosis component 225 may reevaluate the health information 290 to include new medical diagnoses 260 including Condition A and Condition B, which occurs frequently for patients with a predisposition for Condition A. In another instance, the user input 250 may include updated examination information for the patient (for instance, height, weight, lab results, symptom descriptions, diagnostic tests, diagnostic images, or the like). The diagnosis component 225, medical orders component 230 and/or risk assessment component 235 may reevaluate the health information 290 in view of the updated examination information for the patient and may potentially generate updated medical diagnoses 260, medical orders 270 and/or risk assessments 280.

The feedback component 240 may be configured to analyze the health information 290, user input 250, or other information to generate feedback information (or "feedback") in order to update the health information and/or processes used to determine the medical diagnoses 260, medical orders 270 and/or risk assessments 280 based on feedback.

For example, the feedback component 240 may determine that patients with Condition B and with certain demographic information do not have positive treatment outcomes when prescribed Medication D. The feedback component 240 may analyze the medical histories of patients with Condition B to determine treatment outcome patterns and/or user input 250 indicating the relationship between Condition B, the demographic information, and Medication D. Accordingly, the medical orders component 230 may be updated to highlight the relationship between Condition B, the demographic information, and Medication D and/or to determine an alternative medical order 270 that does not include Medication D.

In another example, the feedback component 240 may determine that Physician A prefers to order Test A for patients with Condition C ("historical medical professional information"), although Test A would not be a customary medical order 270 for Condition C. Accordingly, the medical orders component 230 and/or the information or processes associated therewith, may be updated to include a Test A medical order 270 for patients with Condition C when Physician A is the healthcare professional overseeing the patient's care. In this manner, the analysis application 220 may be configured to "learn" in order to improve the accuracy and effectiveness of the medical diagnoses 260, medical orders 270, and/or risk assessments 280.

In some embodiments, the analysis application 220 may be configured to implement security functions to limit access to information within the analysis application, including any regulatory limitations (for instance, according to the Health Insurance Portability and Accountability Act (HIPAA)).

The GUI component 245 may be configured to present information associated with the healthcare information 290 and/or the analysis application 220 on a GUI, such as on a display component of a client logic device 105. FIG. 3 depicts an illustrative health information graphical user interface (GUI) according to an embodiment. As shown in FIG. 3, a health information GUI 300 may include patient information 305, which may generally include information relating to demographics, insurance, payment information, and/or address information for a patient. Healthcare provider information 310 may generally include information relating to current and former healthcare providers associated with the patient, including primary care physicians, specialists, ordering physicians, healthcare providers, healthcare facilities, or the like. Patient vitals and statistics 315 may generally include information relating to various health and/or physical characteristics of a patient, such as height, weight, blood pressure, heart rate, oxygen saturation, BMI, or the like. Physical and diagnostic exams 320 may generally include information relating to physical exams and/or diagnostic exams that a patient has had and/or are currently prescribed, including general physical assessments, abdomen, heart, neck, lungs, extremities, neurological, computed tomography (CT), ultrasound, x-ray, or the like. Health information 325 may generally include information relating to the health information 290 and/or any medical diagnoses 260, medical orders 270 and/or risk assessments 280. In some embodiments, the health information GUI 300 may include separate display elements for medical diagnoses 330, medical orders 335 and/or risk assessments 340. A healthcare professional input 345 element may be configured to allow a healthcare professional to provide user input 250 to the analysis application 220.

In some embodiments, each information display element 305, 310, 315, 320, 325, 330, 335, 340, 345 may be configured to be selected and to display more information as requested by a user. For instance, a user may select the health information 325 display element and the GUI component 245 may provide a window, screen, or other display configuration allowing the user to access a patient's health information 325.

In some embodiments, the GUI component 245 may be configured to highlight, demarcate, color, or otherwise emphasize one or more display elements for various purposes. For example, the GUI component 245 may highlight certain elements that are over a threshold value, such as weight, blood pressure, or the like. In another example, the GUI component 245 may color certain elements based on certain categories, for example, as provided by a healthcare provider. In a further example, the health information used by the diagnosis component 225 to generate a medical diagnosis 260, the medical orders component 230 to generate a medical order 270, or the risk assessment component 235 to generate a risk assessment 280 may be highlighted to allow a healthcare professional to efficiently determine the major factors used to generate the medical assessment. For instance, the GUI component 245 may highlight the blood pressure (BP) 352, the heart exam 354, and the medications 356 of a patient that were used by the diagnosis component 225 to generate a heart condition 358 medical diagnosis 260.

Figure 4:
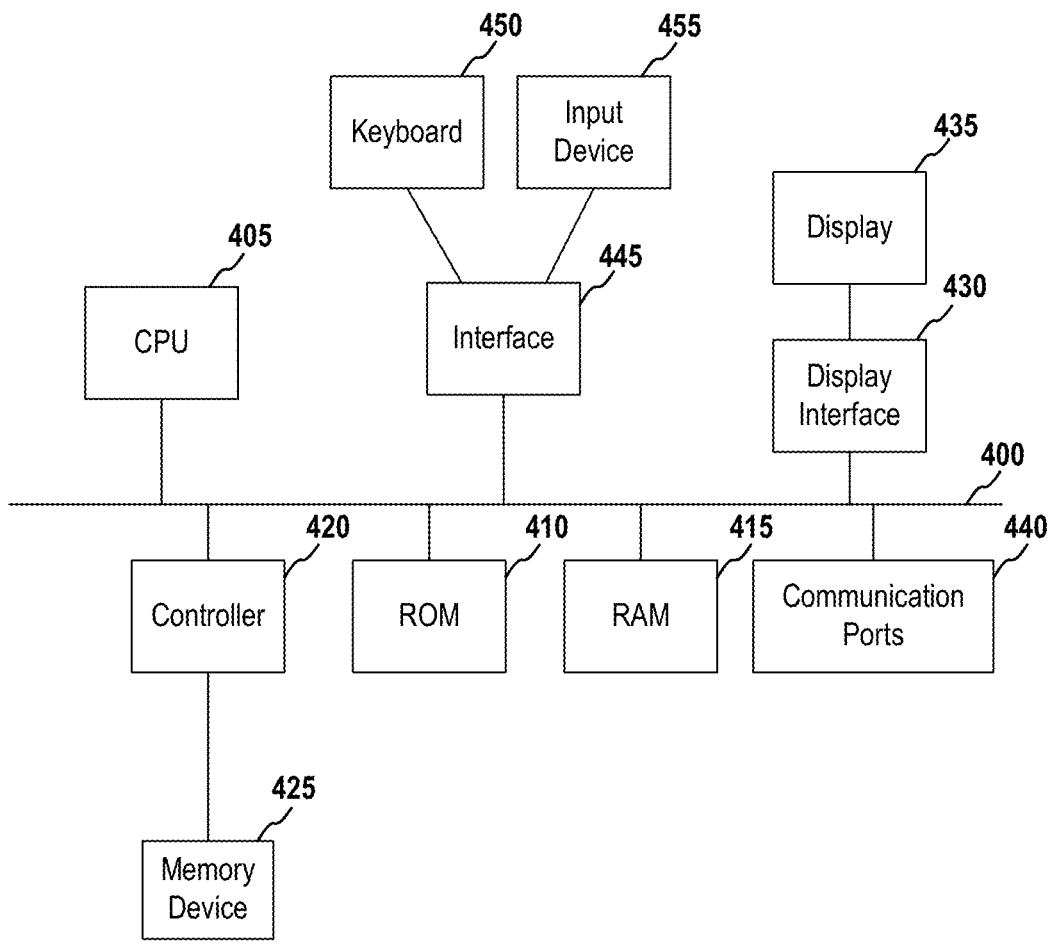
FIG. 4 illustrates various embodiments of a computing device for implementing the various methods and processes described herein.

FIG. 4 depicts a block diagram of exemplary internal hardware that may be used to contain or implement the various computer processes and systems as discussed above. A bus 400 serves as the main information highway interconnecting the other illustrated components of the hardware. CPU 405 is the central processing unit of the system, performing calculations and logic operations required to execute a program. CPU 405, alone or in conjunction with one or more of the other elements disclosed in FIG. 4, is an exemplary processing device, computing device or processor as such terms are used within this disclosure. Read only memory (ROM) 430 and random access memory (RAM) 435 constitute exemplary memory devices.

A controller 420 interfaces with one or more optional memory devices 425 to the system bus 400. These memory devices 425 may include, for example, an external or internal DVD drive, a CD ROM drive, a hard drive, flash memory, a USB drive or the like. As indicated previously, these various drives and controllers are optional devices.

Additionally, the memory devices 425 may be configured to include individual files for storing any software modules or instructions, auxiliary data, common files for storing groups of results or auxiliary, or one or more databases for storing the result information, auxiliary data, and related information as discussed above. For example, the memory devices 425 may be configured to store health information 290 and/or information contained in the data stores 115.

Program instructions, software or interactive modules for performing any of the functional steps associated with the analysis of judicial decision making as described above may be stored in the ROM 430 and/or the RAM 435. Optionally, the program instructions may be stored on a tangible computer-readable medium such as a compact disk, a digital disk, flash memory, a memory card, a USB drive, an optical disc storage medium, such as a Blu-Ray™ disc, and/or other recording medium.

An optional display interface 430 may permit information from the bus 400 to be displayed on the display 435 in audio, visual, graphic or alphanumeric format. Communication with external devices may occur using various communication ports 440. An exemplary communication port 440 may be attached to a communications network, such as the Internet or a local area network.

The hardware may also include an interface 445 which allows for receipt of data from input devices such as a keyboard 450 or other input device 455 such as a mouse, a joystick, a touch screen, a remote control, a pointing device, a video input device and/or an audio input device.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by some embodiments described herein.

What is claimed is:

1. A health information monitoring system comprising:
   a processor; and
   a non-transitory, computer-readable storage medium in operable communication with the processor, wherein the computer-readable storage medium stores one or more programming instructions that, when executed, cause the processor to:
      receive health information associated with a patient, wherein the health information comprises one or more of a physical characteristic, a medical history, at least one symptom, and at least one habit, wherein the medical history comprises medical order history associated with the patient,
      determine, based on the health information, one or more possible diagnoses,
      determine, based on the medical history, at least one diagnosis from the one or more possible diagnoses and at least one treatment,
      score the at least one diagnosis and the at least one treatment based on historical information comprising user generated feedback associated with a plurality of historical patients,
      generate a medical diagnosis based on the score for the at least one diagnosis and the at least one treatment, wherein the medical diagnosis identifies at least one of a disease, an ailment, an injury, a physical condition, and a mental condition,
      compare one or more previous medical orders to the medical history,
      determine one or more applicable medical orders based on the comparison,
      analyze, based on the health information and the historical information, an effectiveness level of the one or more applicable medical orders,
      determine, based on the health information, a complication level of the one or more applicable medical orders,
      determine a medical professional preference level for the one or more applicable medical orders,
      score the at least one physical characteristic,
      analyze the medical history to identify at least one of a diagnosis, a condition, a medication, and a medical procedure,
      score, based on the historical information, the at least one of a diagnosis, a condition, a medication, and a medical procedure,
      score, based on the historical information, the at least one habit,
      generate a risk assessment based on the at least one scored habit, the one or more of the scored physical characteristics, and the score of the least one of a diagnosis, a condition, a medication, and a medical procedure
      generate a medical assessment based on the health information using a plurality of assessment rules, wherein the medical assessment comprises the medical diagnosis, the one or more medical orders, and the risk assessment,
      receive feedback associated with each of the medical diagnosis, the one or more applicable medical orders, and the risk assessment, wherein the feedback comprises:
         user input relating to a medical professional associated with the patient, and
         user input indicating a measure of at least one of accuracy and completeness of the medical assessment, and
      update the historical information and the plurality of assessment rules based on the feedback.

2. The system of claim 1, wherein the computer-readable storage medium contains one or more programming instructions that, when executed, further cause the processor to generate an updated medical assessment responsive to updating the plurality of assessment rules based on the feedback.

3. The system of claim 1, wherein at least a portion of the plurality of assessment rules comprises rules from a third-party source.

4. The system of claim 1, wherein the computer-readable storage medium contains one or more programming instructions that, when executed, further cause the processor to:
   present at least a portion of the health information as a plurality of display elements on a graphical user interface; and
   highlight each of the plurality of display elements that were major factors in generating the medical assessment.

5. The system of claim 1, wherein the computer-readable storage medium contains one or more programming instructions that, when executed, further cause the processor to:
   present at least a portion of the health information as a plurality of display elements on a graphical user interface; and highlight each of the plurality of display elements associated with health information having a value over a predetermined threshold value.

\* \* \* \* \*